United States Patent
Xu

(10) Patent No.: US 11,042,142 B2
(45) Date of Patent: Jun. 22, 2021

(54) INTELLIGENT MULTIFUNCTIONAL STORAGE CABINET DEVICE

(71) Applicant: Suzhou Dusit Technology Co., Ltd, Suzhou (CN)

(72) Inventor: Yijun Xu, Suzhou (CN)

(73) Assignee: SUZHOU DUSIT TECHNOLOGY CO., LTD, Suzhou (CN)

( * ) Notice: Subject to any disclaimer, the term of this patent is extended or adjusted under 35 U.S.C. 154(b) by 139 days.

(21) Appl. No.: 16/600,452

(22) Filed: Oct. 12, 2019

(65) Prior Publication Data

US 2021/0063980 A1    Mar. 4, 2021

(30) Foreign Application Priority Data

Sep. 3, 2019   (CN) .......................... 201910827789.0

(51) Int. Cl.
*G01G 19/00*    (2006.01)
*G05B 19/042*   (2006.01)
(Continued)

(52) U.S. Cl.
CPC ............ *G05B 19/042* (2013.01); *A47B 81/00* (2013.01); *A47J 39/00* (2013.01); *A61L 2/10* (2013.01);
(Continued)

(58) Field of Classification Search
CPC ...... A47B 81/00; A47J 39/00; A61L 2202/11; A61L 2/10; G01G 19/52; G05B 15/02; G05B 19/042; G05B 2219/2648; G06K 7/10366; G08B 21/14; G08B 21/24; G08B 3/10; H04L 67/12; H04N 5/232; H04N 5/23203; H04N 7/18
(Continued)

(56) References Cited

U.S. PATENT DOCUMENTS

2015/0186840 A1* 7/2015 Torres .................... A47F 10/02
                                                      705/339
2017/0208940 A1* 7/2017 Boudreault ............... A47F 3/02
(Continued)

FOREIGN PATENT DOCUMENTS

CA         3064140 A1    11/2018
CN      109637044 A       4/2019

*Primary Examiner* — Naomi J Small
(74) *Attorney, Agent, or Firm* — Bayramoglu Law Offices LLC

(57) ABSTRACT

An intelligent multifunctional storage cabinet device includes a smart cabinet and a backend control terminal, wherein the smart cabinet is connected to and communicates with the backend control terminal via a network connection. The smart cabinet includes a cabinet and a monitoring device. The monitoring device is installed on the top of the cabinet, and the monitoring device is connected to and communicates with the backend control terminal via a network connection. The cabinet includes a parcel storage component comprising a plurality of parcel storage compartments, a food storage component comprising a plurality of food storage compartments, and a key storage component comprising a plurality of key storage compartments. The key storage compartment is located between the parcel storage compartment and the food storage compartment. The parcel storage compartment is located at one side of the food storage compartment.

10 Claims, 2 Drawing Sheets

(51) Int. Cl.
*A47B 81/00* (2006.01)
*A47J 39/00* (2006.01)
*A61L 2/10* (2006.01)
*G01G 19/52* (2006.01)
*G06K 7/10* (2006.01)
*G08B 3/10* (2006.01)
*G08B 21/14* (2006.01)
*G08B 21/24* (2006.01)
*H04L 29/08* (2006.01)
*H04N 5/232* (2006.01)
*H04N 7/18* (2006.01)

(52) U.S. Cl.
CPC .......... *G01G 19/52* (2013.01); *G06K 7/10366* (2013.01); *G08B 3/10* (2013.01); *G08B 21/14* (2013.01); *G08B 21/24* (2013.01); *H04L 67/12* (2013.01); *H04N 5/232* (2013.01); *H04N 7/18* (2013.01); *A61L 2202/11* (2013.01); *G05B 2219/2648* (2013.01); *H04N 5/23203* (2013.01)

(58) Field of Classification Search
USPC ........................................................ 177/245
See application file for complete search history.

(56) References Cited

U.S. PATENT DOCUMENTS

| | | | |
|---|---|---|---|
| 2018/0165636 A1* | 6/2018 | Wilkinson | G01S 19/51 |
| 2018/0197141 A1* | 7/2018 | Venture | G06K 19/07758 |
| 2019/0213212 A1* | 7/2019 | Adato | G06F 16/23 |
| 2020/0012245 A1* | 1/2020 | Marin Pulido | G06Q 50/28 |
| 2020/0160637 A1* | 5/2020 | Hara | G07C 9/33 |
| 2020/0402336 A1* | 12/2020 | Levy | G06Q 10/0838 |

* cited by examiner

INTELLIGENT MULTIFUNCTIONAL STORAGE CABINET DEVICE

TECHNICAL FIELD

The present disclosure relates to the field of smart cabinets, particularly an intelligent multifunctional storage cabinet device.

BACKGROUND

Nowadays, shared smart cabinets are installed in crowded public places such as shopping malls, schools, libraries, public transportation stations, residential quarters among others. Existing smart cabinets come in a variety of types, including courier service drop-boxes, merchandise vending machines, and so on. Although each of these existing smart cabinets serves its purpose, any one type of these existing intelligent cabinets serves only one single purpose and provides only one single simple function of storage. The existing smart cabinets have no other functions such as weighing and detecting the stored items. To sum it up, existing smart cabinets are unable to achieve detection of items, identification of items and intelligent management of items.

SUMMARY

In order to overcome the shortcomings of the prior art, the present disclosure aims to provide an intelligent multifunctional cabinet device, which can solve the problems of identify items and intelligently managing items.

The purpose of the present disclosure is realized by the following technical solution.

An intelligent multifunctional storage cabinet device, comprising a smart cabinet and a backend control terminal, wherein the smart cabinet is connected to and communicates with the backend control terminal via a network connection. The smart cabinet includes a cabinet and a monitoring device. The monitoring device is installed on the top of the cabinet, and the monitoring device is connected to and communicates with the backend control terminal via a network connection. The cabinet includes a parcel storage component comprising a plurality of parcel storage compartments, a food storage component comprising a plurality of food storage compartments, and a key storage component comprising a plurality of key storage compartments. The key storage compartment is located between the parcel storage compartment and the food storage compartment. The parcel storage compartment is located at one side of the food storage compartment. A weighing sensor is installed at the bottom of each parcel storage compartment. The weighing sensor is connected to the backend control terminal via a network connection. The weighing sensor is used for weighing the items in the parcel storage compartment to obtain a weighing result and uploading the weighing result to the backend control terminal. The parcel storage compartment is equipped with an alarm sensor. The alarm sensor is connected to the backend control terminal via a network connection. The alarm sensor detects hazardous items in the parcel storage compartment. The alarm sensor sends out a voice warning signal and transmit an alarm information to the backend control terminal when a user places a hazardous item in the parcel storage compartment. The backend control terminal will, based on the information, send a command to the monitoring device to capture the image of the user as a evidence.

Further, the cabinet includes a display screen. The display screen is located at one side of the food storage compartment and the parcel storage compartment. The display screen is located in the middle of the cabinet. An information input terminal is arranged on the display screen. The information input terminal is connected to the backend control terminal via a network connection. The user can enter the user information which is sent to the backend control terminal through the information input terminal.

Further, a semiconductor heating and cooling device and a temperature sensor are mounted on the sidewall of the food storage compartment. The semiconductor heating and cooling device is connected to the backend control terminal via a network connection. The temperature sensor is connected to the backend control terminal via a network connection. The user can set the temperature through the information input terminal on the display screen. The information input terminal sends the temperature information that is set by the user to the backend control terminal. The backend control terminal receives the real-time temperature information in the food storage compartment detected by the temperature sensor and turns on the heating or cooling function of the semiconductor device according to the real-time detected temperature and the temperature that is set by the user. When the real-time temperature detected by the temperature sensor reaches the temperature that is set by the user, the backend control terminal will send a command to the semiconductor heating and cooling device to stop operating.

Further, a thermal insulation layer is installed on the inner wall of the food storage compartment. The thermal insulation layer is used to provide the heating or cooling function for the food in the food storage compartment.

Further, an ultraviolet lamp is arranged on the inner wall of the food storage compartment. The ultraviolet lamp is located at one side of the thermal insulation layer and is used to sterilize and disinfect the food storage compartment.

Further, a photocatalyst coating is used to cover the outer surface of the thermal insulation layer. A light emitted by the ultraviolet lamp is irradiated on the photocatalyst coating to deodorize, sterilize and disinfect the food storage compartment.

Further, a matrix dirt monitoring system is arranged on the bottom of the food storage compartment. The matrix dirt monitoring system is connected to the backend control terminal via a network connection and is used to detect grease, dirt stains and food residues in the food storage compartment.

Further, the matrix dirt monitoring system includes a plurality of dirt sensors. The dirt sensors are uniformly distributed in a grid format at the bottom of the food storage compartment. When the dirt sensors detect grease, dirt stains and food residues, the dirt sensors send a message to the backend control terminal, and the backend control terminal will then accordingly remind a cleaner to carry out the cleaning work.

Further, the alarm sensor is a gas sensor.

Further, the key storage compartment is equipped with a Radio Frequency Identification (RFID) card reader. The RFID card reader is connected to the backend control terminal via a network connection. When a key containing the RFID chip is placed in the key storage compartment, the RFID card reader reads the information from the RFID chip and transmits the information from the RFID chip to the backend control terminal for matching the key with a specific smart storage compartment.

Compared with the prior art, the beneficial effect of the present disclosure is as follows. An intelligent multifunctional storage cabinet device, comprising a smart cabinet and a backend control terminal, wherein the smart cabinet is connected to the backend control terminal and communicates with the backend control terminal via a network connection. The smart cabinet includes a cabinet and a monitoring device. The monitoring device is installed on the top of the cabinet, and the monitoring device is connected to and communicates with the backend control terminal via a network connection. The cabinet includes a parcel storage component comprising a plurality of parcel storage compartments, a food storage component comprising a plurality of food storage compartments, and a key storage component comprising a plurality of key storage compartments. The key storage compartment is located between the parcel storage compartment and the food storage compartment. The parcel storage compartment is located at one side of the food storage compartment. A weighing sensor is installed at the bottom of each parcel storage compartment. The weighing sensor is connected to the backend control terminal via a network connection. The weighing sensor is used for weighing the items in the parcel storage compartment to obtain a weighing result and uploading the weighing result to the backend control terminal. The parcel storage compartment is equipped with an alarm sensor. The alarm sensor is connected to the backend control terminal via a network connection. The alarm sensor detects hazardous items in the parcel storage compartment. When a user places a hazardous item in the parcel storage compartment, the alarm sensor will send out a voice warning signal and transmit an alarm information to the backend control terminal. The backend control terminal will, based on the alarming information, send a command to the monitoring device to capture the image of the user as a evidence. The weight information of the item in the smart cabinet can be obtained in real time by the weighing sensor. The smart cabinet can store parcels, food, and keys at the same time. The smart cabinet can also detect the hazardous item stored in the smart cabinet, transmit the detected information to the backend control terminal in real time, and send a command to the monitoring device to capture the image of the user as a evidence, which enhances the security of the smart cabinet itself and the items stored inside the cabinet, and satisfies the growing needs of users at the same time.

The above description is only an overview of the technical solution of the present disclosure. In order to have a better understanding of the technical solution of the present disclosure and to implement it according to the content of the specification, the following is a preferred embodiment of the present disclosure in conjunction with the drawings. The present disclosure will be described below in conjunction with the drawings and the specific embodiment.

BRIEF DESCRIPTION OF THE DRAWINGS

The drawings described herein are intended to provide a further understanding of the present disclosure and are part of the present disclosure. The illustrative embodiments of the present disclosure and the description thereof are for explaining the present disclosure and do not constitute an undue limitation of the present disclosure. In the drawings.

In the figures: 1, cabinet; 11, parcel storage compartment; 12, food storage compartment; 13, key storage compartment; 14, display screen; 2, monitoring device.

DETAILED DESCRIPTION OF THE EMBODIMENTS

The present disclosure will now be further described in detail in conjunction with the drawings and specific embodiments. It should be noted that, under the premise of non-conflict, the following embodiments or the following technical features may be arbitrarily combined to form a new embodiment.

Figure 1:
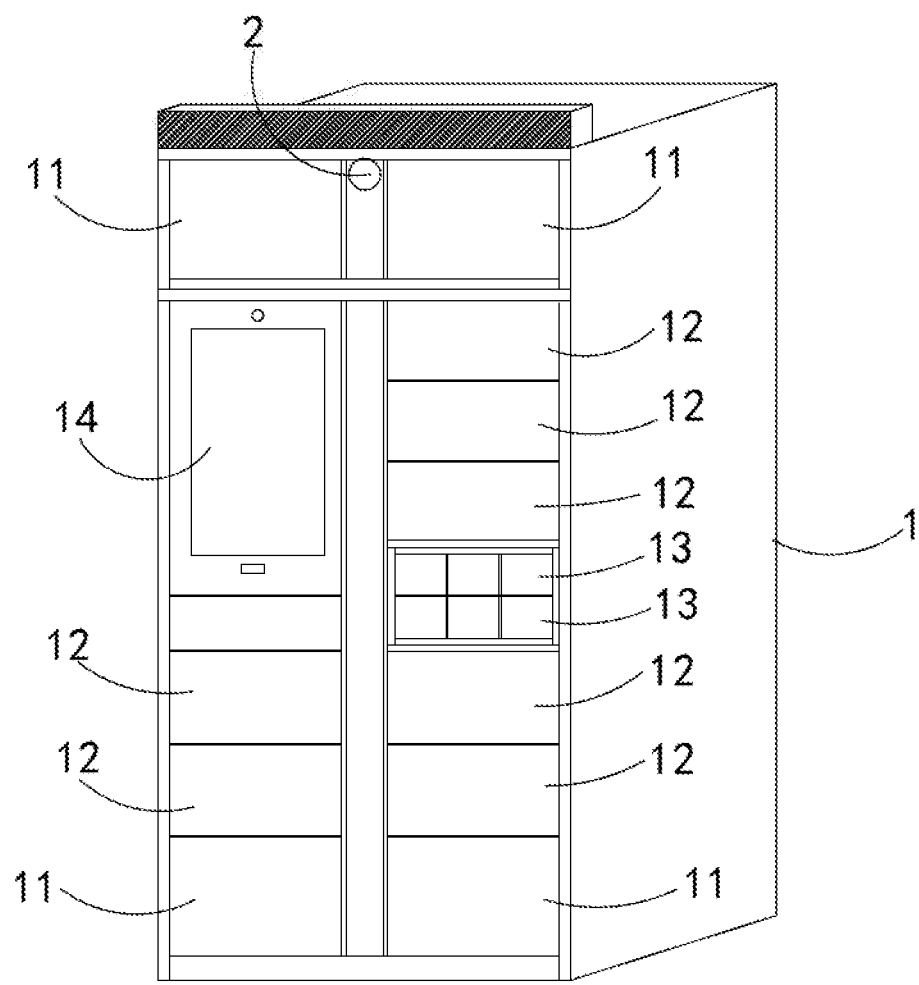
FIG. 1 is a structural schematic diagram of an intelligent multifunctional storage cabinet device of the present disclosure.
Figure 2:
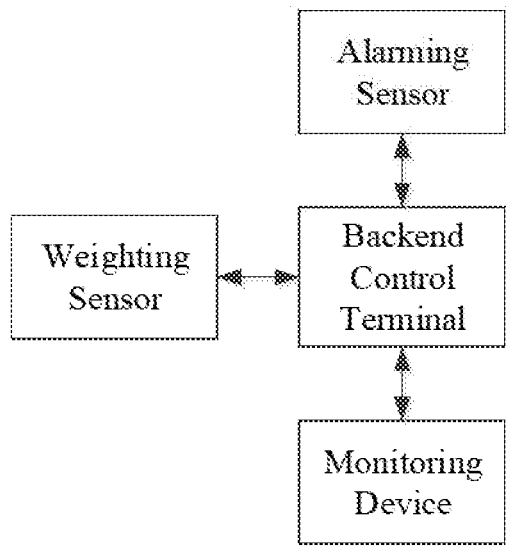
FIG. 2 is a schematic diagram showing the connection of some control devices in a parcel storage compartment of an intelligent multifunctional storage cabinet device of the present disclosure.
Figure 3:
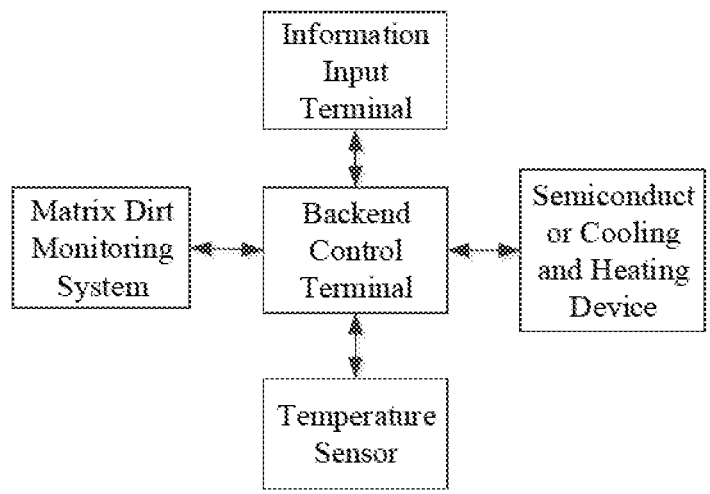
FIG. 3 is a schematic diagram showing the connection of control devices in a food storage compartment in an intelligent multifunctional storage cabinet device of the present disclosure.
Figure 4:
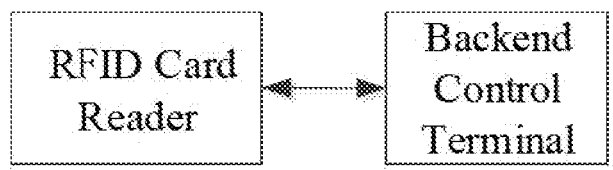
FIG. 4 is a schematic diagram showing the connection of some control devices in a key storage compartment in an intelligent multifunctional storage cabinet device of the present disclosure.

As shown in FIGS. 1-4, an intelligent multifunctional storage cabinet device of the present application includes a smart cabinet and a backend control terminal. The smart cabinet is connected to and communicates with the backend control terminal via a network connection. The smart cabinet includes the cabinet 1 and the monitoring device 2. The monitoring device 2 is installed on the top of the cabinet 1. The monitoring device 2 is a camera, which can capture facial images in real time.

The monitoring device 2 is connected to the backend control terminal via a network connection. The cabinet 1 includes a parcel storage component comprising a plurality of parcel storage compartments 11, a food storage component comprising a plurality of food storage compartments 12, and a key storage component comprising a plurality of key storage compartments 13. On the doors of each of the parcel storage compartments 11, each of the food storage compartments 12 and each of the key storage compartments 13 are installed with a corresponding door lock controller. All the door lock controllers are connected to the backend control terminal via a network connection for controlling the opening and closing of the compartment doors. The key storage compartment 13 is located between the parcel storage compartment 11 and the food storage compartment 12. The parcel storage compartment 11 is located at one side of the food storage compartment 12. A weighing sensor is installed at the bottom of each parcel storage compartment 11. The weighing sensor is connected to the backend control terminal via a network connection. The weighing sensor is used for weighing the items in the parcel storage compartment 11 to obtain a weighing result and uploading the weighing result to the backend control terminal. The parcel storage compartment 11 is equipped with an alarm sensor. In the present embodiment, the alarm sensor is a gas sensor. The gas sensor is a converter that converts the volume fraction of a certain gas into a corresponding electrical signal and may be used to detect hazardous gases in the parcel. In the present application, the gas sensor may be an electrochemical gas sensor, or a catalytic combustion type gas sensor, or a thermally conductive gas sensor, or an infrared gas sensor, or a solid electrolyte gas sensor. The gas sensor is used to detect hazardous items in the parcel storage compartment 11. The alarm sensor is connected to the backend control terminal via a network connection. When a user places a hazardous item in the parcel storage compartment 11, the alarm sensor will send out a voice warning signal and transmit an alarm information to the backend control terminal. The backend control terminal will, based on the alarming information, send a command to the monitoring device 2 to capture the image of the user as a evidence. The backend control terminal stores the images that is captured by the monitoring device 2 and sends the images to the alarm terminal to report to the police.

In the present embodiment, the cabinet 1 further includes the display screen 14. The display screen 14 is located at one side of the food storage compartment 12 and the parcel storage compartment 11. The display screen 14 is located in the middle of the cabinet 1. An information input terminal is arranged on the display screen. The information input terminal is connected to the backend control terminal via a network connection. Through the information input terminal, the user can enter the user information which is sent to the backend control terminal. The user information entered by the user includes, but is not limited to, a fingerprint and a facial image. The user can create a user account through the information input terminal and set the login password to log in. The login password may be a fingerprint, a facial image or an account password. The user information is stored in the backend control terminal. The user can store in or remove the parcel in the smart cabinet, by entering the fingerprint, facial image, or an account password.

A semiconductor heating and cooling device and a temperature sensor are mounted on the sidewall of the food storage compartment 12. The semiconductor heating and cooling device performs functions of cooling and heating. The semiconductor heating and cooling device is connected to the backend control terminal via a network connection. The temperature sensor is connected to the backend control terminal via a network connection. The user can set the temperature through the information input terminal on the display screen. The information input terminal sends the information of the temperature that is set by the user to the backend control terminal. The backend control terminal receives the real-time information of the temperature in the food storage compartment 12 detected by the temperature sensor and turns on the heating or cooling function of the semiconductor heating and cooling device according to the real-time temperature and the temperature that is set by the user. When the real-time temperature detected by the temperature sensor reaches the temperature that is set by the user, the backend control terminal will send a command to the semiconductor heating and cooling device to stop operating. A thermal insulation layer is installed on the inner wall of the food storage compartment 12. The thermal insulation layer is used to provide the heating or cooling function for the food in the food storage compartment 12. In the present embodiment, the thermal insulation layer is an insulating foam layer. In the present embodiment, the thermal insulation layer contains magnetic materials which can be magnetically drawn into the food storage compartment 12 for easy replacement. An ultraviolet lamp is arranged on the inner wall of the food storage compartment 12. The ultraviolet lamp is located at one side of the thermal insulation layer and is used to sterilize and disinfect the food storage compartment. A photocatalyst coating covers over the outer surface of the thermal insulation layer. A light emitted by the ultraviolet lamp is irradiated on the photocatalyst coating to deodorize, sterilize, and disinfect the food storage compartment. A matrix dirt monitoring system is arranged on the bottom of the food storage compartment 12. The matrix dirt monitoring system is connected to the backend control terminal via a network connection and is used to detect grease, dirt stains and food residues in the food storage compartment 12. The matrix dirt monitoring system includes a plurality of dirt sensors. In the present embodiment, the dirt sensors are conductive wires. When a stain occurs, the related conductive wire region will trigger the control circuit to make the whole circuit closed and send warning and alarm information. The dirt sensors include, but are not limited to, multiple wires distributed uniformly in a grid format at the bottom of the food storage compartment 12. When the dirt sensors detect grease stains and food residues, the dirt sensors send a signal to the backend control terminal, and the backend control terminal will then accordingly remind a cleaner to carry out the cleaning work.

In the present embodiment, the key storage compartment 13 is equipped with a RFID card reader. The RFID card reader is connected to the backend control terminal via a network connection. When a key containing the RFID chip is placed in the key storage compartment 13, the RFID card reader reads the information from the RFID chip and transmits the information from the RFID chip to the backend control terminal for matching the key with a specific smart storage compartment. Before using the key storage compartment 13, the user needs to register with the backend control terminal by entering and sending user information to the backend control terminal. The user information includes, but is not limited to, building name, floor number, and room number, etc. Based on the user information, the backend control terminal will bind the key storage compartment 13 to the user information and create a RFID chip based on the user information. Each user information corresponds to a key storage compartment 13. The RFID chip will be installed on the key of the corresponding user. When the user needs to use the key storage compartment 13, the key is placed in the key storage compartment 13, and the RFID card reader in the key storage compartment 13 reads the information from the RFID chip and sends the information from the RFID chip to the backend control terminal for matching the key with a specific smart storage compartment. The backend control terminal will match the received information with the information in the corresponding RFID chip in the key storage compartment 13. If the matching is successful, the backend control terminal will send a command to the door lock controller on the key storage compartment 13 to close the door of the key storage compartment 13.

An intelligent multifunctional storage cabinet device of the present application includes a smart cabinet and a backend control terminal, wherein the smart cabinet is connected to and communicates with the backend control terminal via a network connection. The smart cabinet includes the cabinet and the monitoring device. The monitoring device is installed on the top of the cabinet. The monitoring device is connected to and communicates with the backend control terminal via a network connection. The cabinet includes the parcel storage component comprising the plurality of parcel storage compartments, the food storage component comprising the plurality of food storage compartments, and the key storage component comprising the plurality of key storage compartments. The key storage compartment is located between the parcel storage compartment and the food storage compartment. The parcel storage compartment is located at one side of the food storage compartment. The weighing sensor is installed at the bottom of each parcel storage compartment. The weighing sensor is connected to the backend control terminal via a network connection. The weighing sensor is used for weighing the items in the parcel storage compartment to obtain a weighing result and uploading the weighing result to the backend control terminal. The parcel storage compartment is equipped with an alarm sensor. The alarm sensor is connected to the backend control terminal via a network connection. The alarm sensor is used to detect hazardous items stored in the parcel storage compartment. When a user places an item in the parcel storage compartment, if the item is a hazardous item, the alarm sensor will send out a voice warning and transmit the alarm information to the backend control terminal. The backend control terminal will, based on the alarm information, send a command to the monitoring device to capture the image of the user as a evidence. The weight information of the item in the smart cabinet can be obtained in real time by the weighing sensor. The smart cabinet can store parcels, food, and keys at the same time. The smart cabinet can also detect the hazardous item stored in the smart cabinet, transmit the detected information to the backend control terminal in real time, and send a command to the monitoring device to capture the images of the user as a evidence, which enhances the security of the smart cabinet itself and the items stored inside the cabinet, and satisfies the growing needs of users at the same time. While storing the food, the food can be heated or cooled, and the stored food can be effectively sterilized, disinfected, and deodorized in the smart cabinet. If the food is placed in the food storage compartment for an extended amount of time and displays grease stains and food residues, the smart cabinet can promptly alarm and arrange for a cleaner to carry out the cleaning work, thereby ensuring the safety of the food and the overall cleanliness of the smart cabinet itself.

The preferred embodiment of the present disclosure, are not intended to limit the scope of the present disclosure in any way. Those skilled in the art can easily implement the present disclosure as shown in the drawings and the preferred embodiments. However, any equivalent variations of changes, modifications, and evolutions made by one skilled in the art using the technical content disclosed herein, without departing from the technical scope of the present disclosure, are equivalent embodiments of the present disclosure. Any changes, modifications, and evolutions of any equivalent changes made to the preferred embodiment disclosed herein, in accordance with the elemental techniques of the present disclosure, are within the scope of protection of the technical solutions of the present disclosure.

The invention claimed is:

1. An intelligent multifunctional storage cabinet device, comprising a smart cabinet and backend control terminal, wherein die smart cabinet is connected to and communicates with the backend control terminal via a network connection; the smart cabinet comprises a cabinet and a monitoring device; the monitoring device is installed on the top of the cabinet; the monitoring device is connected to and communicates with the backend control terminal Via a network connection; the cabinet comprises a parcel storage component comprising a plurality of parcel storage compartments, a food storage component comprising a plurality of food storage compartments, and a key storage component comprising a plurality of key storage compartments; the key storage compartment is located between the parcel storage compartment and the food storage compartment; the parcel storage compartment is located at one side of the food storage compartment; a weighing sensor is installed at the bottom of each parcel storage compartment; the weighing sensor is connected to the backend control terminal via a network connection; the weighing sensor is used for weighing the items in the parcel storage compartment to obtain a weighing result and uploading the weighing result to the backend control terminal; die parcel storage compartment is equipped with an alarm sensor; die alarm sensor is connected to the backend control terminal via a network connection; the alarm sensor detects hazardous items in the parcel storage compartment; the alarm sensor sends out a voice warning and transmit an alarm information to the backend control terminal when a user places a hazardous item in the parcel storage compartment; the backend control terminal will, based on the alarm information, send a command to die monitoring device to capture the image of the user as evidence.

2. The intelligent multifunctional storage cabinet device according to claim 1, wherein the cabinet further comprises a display screen; the display screen is located at one side of the food storage compartment and the parcel storage compartment; the display screen is located in the middle of the cabinet, an information input terminal is arranged on the display screen; the information input terminal is connected to the backend control terminal via a network connection; a deliveryman can enter an information about user and food, and the information is sent to the backend control terminal through the information input terminal.

3. The intelligent multifunctional storage cabinet device, according to claim 2, wherein a semiconductor heating and cooling device and a temperature sensor are mounted on the sidewall of the food storage compartment; the semiconductor heating and cooling device is connected to the backend control terminal via a network connection; the temperature sensor is connected to the backend control terminal via a network connection; a deliveryman can enter information about food through the information input terminal, and the information input terminal sends the food information to the backend control terminal; the backend control terminal receives the real-time temperature information in the food storage compartment detected by the temperature sensor and automatically turns on the heating or cooling function of the semiconductor device, according to the real-time detected temperature and the the temperature that is set by the user; when the real-time temperature detected by the temperature sensor reaches the temperature that is set by the user, the backend control terminal will send a command to the semiconductor heating and cooling device to stop operating.

4. The intelligent multifunctional storage cabinet device according to claim 1, wherein a thermal insulation layer is installed on the inner wall of the food storage compartment, and the thermal insulation layer is used to provide the heating or cooling function for the food in the food storage compartment.

5. The intelligent multifunctional storage cabinet device according to claim 4, wherein an ultraviolet lamp is arranged on the inner wall of the food storage compartment; the ultraviolet lamp is located at one side of the thermal insulation layer and is used to sterilize and disinfect the food storage compartment.

6. The intelligent multifunctional storage cabinet device according to claim 5, wherein a photocatalyst coating is used to cover the outer surface of the thermal insulation layer; a light emitted by the ultraviolet lamp is irradiated on the photocatalyst coating to deodorize, sterilize and disinfect the food storage compartment.

7. The intelligent multifunctional storage cabinet device according to claim 1, wherein a matrix dirt monitoring system is arranged on the bottom of the food storage compartment; the matrix dirt monitoring system is connected to the backend control terminal via a network connection and is used to detect grease stains and food residues in the food storage compartment.

8. The intelligent multifunctional storage cabinet device according to claim 7, wherein the matrix dirt monitoring system comprises a plurality of dirt sensors; the dirt sensors are uniformly distributed in a grid format at the bottom of the food storage compartment; when the dirt sensors detect grease, dirt stains and food residues, the dirt sensors will send a message to the backend control terminal, and the backend control terminal will then accordingly remind a cleaner to carry out the cleaning work.

9. The intelligent multifunctional storage cabinet device according to claim 1, wherein the alarm sensor is a gas sensor.

10. The intelligent multifunctional storage cabinet device according to claim 1, wherein the key storage compartment is equipped with a Radio Frequency Identification (RFID) card reader; the RFID card reader is connected to the backend control terminal via a network connection; when a key containing the RFID chip is placed in the key storage compartment, the RFID card reader reads the information from the RFID chip and transmits the information from the RFID chip to the backend control terminal for matching the key with a specific smart storage compartment.

\* \* \* \* \*